US006458923B1

(12) United States Patent
Kyle

(10) Patent No.: US 6,458,923 B1
(45) Date of Patent: Oct. 1, 2002

(54) MODIFIED POSITION (7) BRADYKININ ANTAGONIST PEPTIDES

(75) Inventor: Donald James Kyle, Abington, MD (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 08/302,988

(22) Filed: Sep. 12, 1994

Related U.S. Application Data

(63) Continuation of application No. 07/981,530, filed on Nov. 25, 1992, now abandoned, which is a continuation-in-part of application No. 07/805,640, filed on Dec. 12, 1991, now abandoned.

(51) Int. Cl.$^7$ .................. A61K 38/00; C07K 16/00; C07K 17/00; C07K 7/00
(52) U.S. Cl. .................. 530/314; 530/328; 530/335; 530/336; 530/337; 530/408; 530/807; 530/816; 514/2; 514/15; 514/803
(58) Field of Search .................. 530/314, 328, 530/408, 807, 816, 336, 335, 337; 514/15, 2, 803

(56) References Cited

U.S. PATENT DOCUMENTS

| | | | |
|---|---|---|---|
| 4,242,329 A | 12/1980 | Claeson et al. | 424/177 |
| 4,483,850 A | 11/1984 | Patchett et al. | 424/177 |
| 4,693,993 A | 9/1987 | Stewart et al. | 514/14 |
| 4,801,613 A | 1/1989 | Stewart et al. | 514/14 |
| 4,822,894 A | 4/1989 | Geiger et al. | 548/252 |
| 4,923,963 A | 5/1990 | Stewart et al. | 530/314 |

FOREIGN PATENT DOCUMENTS

| | | |
|---|---|---|
| WO | 0 370 453 | 5/1990 |
| WO | 0 413 277 | 2/1991 |
| WO | 0 472 220 | 2/1992 |

OTHER PUBLICATIONS

Karanewsky et al., "(Phosphinyloxy) acyl Amino Acid Inhibitors of Angiotensin Converting Enzyme. 2. Terminal Amino Acid Analogues of (S)–1–[6–Amino–2–[[hydroxy (4–phenylbutyl)phosphinyl]oxy]–1–oxohexyl]–L–proline," *Journal of Medicinal Chemistry*, vol. 33, No. 5 (1990), pp. 1459–1469.

Smith et al., "Synthesis and Pharmacological Activity of Angiotensin Converting Enzyme Inhibitors: N–(Mercaptoacyl)–4–substituted—(S)—prolines," *Journal of Medicinal Chemistry*, vol. 31, No. 4 (1988), pp. 875–885.

Krapcho et al., "Angiotensin–Converting Enzyme Inhibitors. Mercaptan, Carboxyalkyl Dipeptide, and Phosphinic Acid Inhibitors Incorporating 4–Substituted Prolines," *Journal of Medicinal Chemistry*, vol. 31, No. 6 (1988), pp. 1148–1160.

Hock et al., "Hoe 140 a new potent and long acting bradykinin–antagonist: in vitro studies", *Br. J. Pharmacol.*, vol. 102, pp. 769–773 (1991).

Wirth et al., "Hoe 140 a new potent and long acting bradykinin–antagonist: in vitro studies", *Br. J. Pharmacol.*, vol. 102, pp. 774–777 (1991).

Pongracic et al., "A competitive kinin receptor antagonist, [DArg$^0$, Hyp$^3$, DPhe$^7$]–bradykinin, does not affect the response to nasal provocation with bradykinin", *–Br. J. Clin. Pharmacol.*, vol. 31, pp. 287–294 (1981).

Higgins et al., "A study of the efficacy of the bradykinin antagonist, NPC 567, in rhinovirus infections in human volunteers", *Chemical Abstracts*, 190 114: 220805d (1991).

Soler et al., "A Bradykinin Antagonist Modifies AntigenInduced Airway Hyper–responsiveness and Airway Inflammation in Allergic Sheep", *Am. Rev. Respir. Dis.*, vol. 137, A327 (1989).

John M. Stewart, "Hydroxyproline Analogs of Bradykinin", *Journal of Medicinal Chemistry*, vol. 17, No. 5, pp. 537–539 (1974).

J.M. Stewart, "Chemistry and Biologic Activity of Peptides Related to Bradykinin", *Handbook of Experimental Pharmacology*, vol. XXV Supplement, Springler–Verlag Berlin Heidelberg (1979).

J. Barabe et al., "New agonist and antagonist analogues of bradykinin", *Can. J. Physiol. Pharmacol.*, vol. 62, pp. 627–629 (1984).

Raymond J. Vavreck et al., "Smooth Muscle Selectivity in Bradykinin Analogs with Multiple D–Amino Acid Substitutions", Department of Biochemistry, University of Colorado School of Medicine, pp. 543–547.

J. Rifo et al., "Bradykinin receptor antagonists used to characterize the heterogeneity of bradykinin–induced responses i rat vas deferens", *European Journal of Pharmacology*, vol. 142, pp. 305–312 (1987).

I.J. Zeitlin et al., "Mobilization of tissue kallikrein in inflammatory disease of the colon", Wolfson Laboratories, Gastrointestinal Unit, Western General Hospital, and the Department of Clinical Surgery, University of Edinburgh, pp. 133–138, (1972).

Kenji Suzuki et al., "Synthesis of Every Kinds of Peptide Fragments of Bradykinin", *Chem. Pharm. Bull.*, vol. 17, No. 8, pp. 1671–1678 (1969).

D. Kyle et al., "Probing the Bradykinin Receptor: Mapping the Geometric Topography Using Ethers of Hydroxyproline in Novel Peptides", *J. Med. Chem.*, vol. 34, pp. 2649–2653 (1991).

*Primary Examiner*—Jyothsna Venkat
*Assistant Examiner*—Tomas Friend
(74) *Attorney, Agent, or Firm*—Nath & Associates PLLC; Gary M. Nath; Todd L. Juneau

(57) ABSTRACT

The substitution of the L-Pro at the 7-position of the peptide hormone bradykinin or other substituted analogs of bradykinin with an isoquinoline derivative which converts bradykinin agonists into bradykinin antagonists. The invention further includes the novel 7-position modified bradykinin antagonists which increase enzyme resistance, antagonist potency, and/or specificity of the new bradykinin antagonists. The analogs produced are useful in treating conditions and diseases of a mammal and human in which an excess of bradykinin or related kinins are produced or injected as by insect bites.

4 Claims, No Drawings

MODIFIED POSITION (7) BRADYKININ ANTAGONIST PEPTIDES

RELATED APPLICATIONS

This application is a continuation of U.S. patent application Ser. No. 07/981,530, filed Nov. 25, 1992, now abandoned, which is a continuation-in-part (CIP) of U.S. patent application Ser. No. 07/805,640, filed Dec. 12, 1991, now abandoned, the entire contents of which applications are hereby incorporated in their entirety.

BACKGROUND OF THE INVENTION

1. Field of the Invention

This invention relates to compounds which are bradykinin receptor antagonists, pharmaceutical compositions and methods for using these compounds to antagonize the effects of bradykinin in mammals, including humans. More particularly, the invention relates to the substitution of the L-Pro at position 7 with an isoquinoline derivative which converts bradykinin agonists into antagonists and also includes additional modifications at other positions within the 7-position modified bradykinin antagonist which confer increased antagonist potency, resistance to enzymatic degradation and/or tissue specificity on the D-amino acid-containing bradykinin sequence.

2. Description of the Prior Art

Bradykinin (BK) is a nonapeptide generated as a result of the activity of kallikreins, a group of proteolytic enzymes present in most tissues and body fluids, on kininogens. Once released, kinins produce many physiological responses, including pain and hyperalgesia by stimulating C- and A-fibers in the periphery. There is also considerable evidence that kinins contribute to the inflammatory response.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via stimulation by bradykinin of the activation of the arachidonic acid pathway which produces prostaglandins and leukotrienes, the more distal and actual mediators of inflammation.

In addition to its algesic and proinflammatory effects, bradykinin is a vasodilator. Because of its ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

Thus, a bradykinin inhibitor or bradykinin receptor antagonist is expected to posses a number of desirable biological effects in the treatment, for example, of inflammation, septic shock, asthma, burn pain, rhinitis and allergy.

The search for understanding the mechanism of action of bradykinin, which is essential for the development of useful tools for diagnostic use, and for the development of therapeutic agents aimed at alleviating the intense pain caused by the production and overproduction of bradykinin, has been hindered by the lack of specific sequence-related competitive antagonists of bradykinin.

Several non-peptide, non-specific and non-selective antagonists of one or more of the biological activities of bradykinin have been described among compounds as diverse as analgesics and anti-inflammatory substances, which act via the prostaglandin system and not directly on bradykinin biological receptors. These are antihistamines; bradykinin-antibodies; benzodiazepine derivatives; high molecular weight ethylene oxide polymers; gallic acid esters and serotonin inhibitors. None of these compounds or classes of compounds specifically inhibit bradykinin.

Heptyl esters of various amino acid-containing substances, such as single basic amino acids, the dipeptide Phe-Gly and of analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Preparations of damaged vascular tissue have been reported to respond to bradykinin analogs which lack the C-terminal arginine residue, but not to bradykinin itself, and analogs of these des-Arg(9)-bradykinins have been developed as antagonists for the non-physiological activity of bradykinin. These antagonists have no significant bradykinin-like agonist effects, nor any antagonist effect on any of the physiologically significant kinin-responding systems. Furthermore, several bradykinin analogs containing the O-methyl ether of Tyr residues at positions 5 and/or 8 have been reported to produce mixed agonist/antagonist activity on isolated uteri of galactosemic rats, but not on normal rats.

Other changes in the bradykinin molecule have been additions of amino acids at the N-terminal end which affect the rate of enzymatic degradation of bradykinin in vivo.

It has been reported that the half life of bradykinin in the systemic circulation is less than 30 seconds. Bradykinin appears to be completely destroyed (98–99% destruction) on a single passage through the pulmonary circulation as determined in an anesthetized rat by measuring the depressor effects of an agonist following intra-aortic (IA) (bypassing the pulmonary circulation) and intravenous (IV) administration. Resistance of bradykinin agonists to pulmonary kininase destruction in vivo also appears promoted by addition of single (i.e., D-Arg-, D-Lys-, Lys-) and double (D-Lys-Lys-) basic amino acid residues to the N-terminal of the bradykinin sequence. The addition of the dipeptide Lys-Lys to the N-terminal of bradykinin agonists has been reported to confer complete resistance to in vivo destruction on initial passage through the pulmonary circulation.

Several research groups have prepared bradykinin receptor antagonists. Stewart and Vavrek in U.S. Pat. No. 4,801, 613, (which reference is incorporated in its entirety herein) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The analogs produced are useful in treating conditions and diseases of a mammal and human in which an excess of bradykinin or related kinins are produced or injected as by insect bites into the body. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY.

In U.S. Pat. No. 4,693,993, also to Stewart and Vavrek, additional L-Pro substitution materials are disclosed.

U.S. Pat. No. 4,242,329 to Claeson et al. disclose the formation of Bradykinin-inhibiting tripeptide derivatives. A process for producing said tripeptide derivatives by synthesis and purification methods which are known in peptide chemistry is also disclosed as well as pharmaceutical preparations comprising the tripeptide derivative.

Published European Patent Application No. 0 413 277 A1 discloses bradykinin antagonists. The letters disclosed represent natural or synthetic amino acids including ring-constrained heterocyclic amino acids (e.g., spiro(bicycl [2.2.1]heptan)-2,3-pyrrolidin-5-carboxylic acid) wherein the peptides were prepared using standard solid phase FMOC technology.

SUMMARY OF THE INVENTION

The present invention resides in the discovery that the novel compounds identified below, are potent bradykinin receptor antagonists. The compounds are useful in the treatment of various diseases including inflammatory disorders, asthma, septic shock and burn pain. Included in the invention are pharmaceutical compositions containing the inventive compounds and methods of using the compounds as bradykinin receptor antagonists.

More particularly, the invention relates to the modification of the sequence of the mammalian peptide hormone bradykinin (Arg Pro Pro Gly Phe Ser Pro Phe Arg), SEQ ID No. 1, and pharmaceutically acceptable salts thereof, at the Pro residue at position 7 in a unique manner which produces sequence-related analogues that act a specific and competitive inhibitors of the biological activities of bradykinin. The invention specifically relates to the substitute of the L-Pro at position 7 with a material having a D-configuration and the formula selected from the group consisting of:

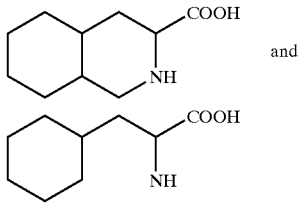

and

The free carboxylic acid forms of the compound have been abbreviated D-Ric and beta-cyclohexylalanine respectively.

More specifically, the invention relates to the formation of peptides having the formula:

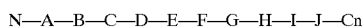

wherein

N is hydrogen;

A and B are independently selected from the group consisting of L-Arg, D-Arg, D-Gln, L-Gln, D-Asn, L-Asn, N-ε-acetyl-D-lysine, ε-acetyl-L-lysine, $N^G$-p-tosyl-Arg, $N^G$-nitro-Arg, Lys-Lys, acetyl-D-Arg, L-citrulline, L-Lys, and D-Lys;

C and D are a direct bond or are independently selected from the group consisting of Pro, dehydroPro, hydroxyPro, Tic, Aoc, L-azetidine-2-carboxylic acid, Eac, Gly, Thz, Oic, and Aib;

E is a direct bond or is selected from the group consisting of Gly, Ala, Thr, and Ser;

F is selected from the group consisting of Phe, Thi, Leu, Ile, Tic, Oic, homophe, phenylGly, β-cyclohexylalanine, Nal, and Val;

G is a direct bond or is selected from the group consisting of Ser, Thr, hydroxypro, Gly, Val, and Ala;

H is a compound of the D-configuration having the formula selected from the group consisting of:

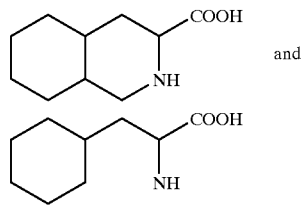

and

I is selected from the group consisting of Oic, Aoc, Thz, Tic, hype (t-sph), hype (c-sph), hype (c-pr), hype (t-pr) L-indoline-2-carboxylic acid, octahydro-1H-isoindole-1-carboxylic acid, pipecolinic acid, Pro, hydroxypro, azetidine-2-carboxylic acid, Aib, Leu, Ile, Val, Thi, and Phe;

J is selected from the group consisting of Arg, Orn, Asn, Gln, N-ε-acetyl-Lys, N-δ-acetyl-Orn, and Lys;

n is a hydroxyl group or a C-terminal extension such as an amide, alkoxy group, an acidic, basic or neutral aliphatic, aromatic, or cyclic amino acid residue of the D- or L-configuration or a peptide extension composed of D- or L-amino acids; and pharmaceutically acceptable salts thereof.

A particularly preferred material is a peptide wherein:

N is hydrogen;

A and B are independently selected from the group consisting of L-Arg, D-Arg, Lys-Lys, Lys;

C and D are independently selected from the group consisting of Pro, dehydroPro, and hydroxyPro;

E is Gly;

F is selected from the group consisting of Phe, Thi, Leu, and β-cyclohexylalanine;

G is a direct bond or is selected from the group consisting of Ser and Thr;

H is a compound of the D-configuration having the formula selected from the group consisting of:

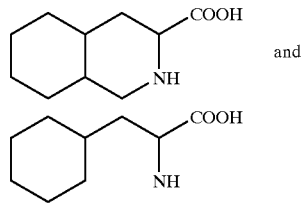

and

I is selected from the group consisting of Oic, Aoc, Thz, Pro, hype (t-sph), hype (c-sph), hype (c-pr), hype (t-pr), pipecolinic acid, Leu, Phe, Thi, and Tic;

J is selected from the group consisting of Arg and Lys;

Cn is a hydroxyl group;

and pharmaceutically acceptable salts thereof.

Another preferred material is a peptide wherein:

N is hydrogen;

A is D-Arg;

B is Arg;

C is Pro;

D is selected from the group consisting of Pro and HydroxyPro;

E is Gly;

F is selected from the group consisting of Phe, Leu, and Thi;

G is a direct bond or is Ser;

H is a compound of the D-configuration having the formula selected from the group consisting of:

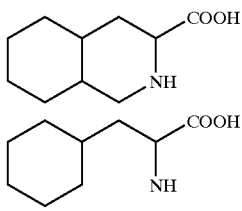

I is selected from the group consisting of OIC, AOC and Tic, hype (t-sph), hype (c-sph), hype (c-pr), hype (t-pr), J is Arg;

Cn is a hydroxyl group;

and pharmaceutically acceptable salts thereof.

Another embodiment of the invention involves a pharmaceutical composition useful as a bradykinin receptor antagonist comprising a pharmaceutical carrier and an effective amount of the novel bradykinin-type peptide. The invention also involves a process for antagonizing bradykinin receptor activity in mammals which comprises: administering to a subject an effective amount of the novel compound to antagonize bradykinin receptor activity.

A further embodiment involves a pharmaceutical preparation for treating local pain and inflammation from burns, wounds, cuts, rashes, and other such trauma and pathological conditions caused by the production of bradykinin or related kinins by an animal which comprises administering an effective amount of the novel bradykinin type peptide sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

As discussed above, the present compounds are modified position (7) bradykinin receptor antagonists having the following formula:

N—A—B—C—D—E—F—G—H—I—J-Cn wherein

N is hydrogen;

A and B are independently selected from the group consisting of L-Arg, D-Arg, D-Gln, L-Gln, D-Asn, L-Asn, N-$\epsilon$-acetyl-D-lysine, $\epsilon$-acetyl-L-lysine, $N^G$-p-tosyl-Arg, $N^G$-nitro-Arg, Lys-Lys, acetyl-D-Arg, L-citrulline, L-Lys, and D-Lys;

C and D are a direct bond or are independently selected from the group consisting of Pro, dehydroPro, hydroxyPro, Tic, Aoc, L-azetidine-2-carboxylic acid, Eac, Gly, Thz, Oic, and Aib;

E is a direct bond or is selected from the group consisting of Gly, Ala, Thr, and Ser;

F is selected from the group consisting of Phe, Thi, Leu, Ile, Tic, Oic, homoPhe, phenylGly, β-cyclohexylalanine, and Nal;

G is a direct bond or is selected from the group consisting of Ser, Thr, hydroxyPro, Gly, Val, and Ala;

H is a compound of the D-configuration having the formula selected from the group consisting of:

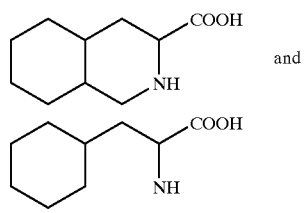

I is selected from the group consisting of Oic, Aoc, Thz, Tic, hype (t-sph), hype (c-sph), hype (c-pr), hype (t-pr), L-indoline-2-carboxylic acid, octahydro-1H-isoindole-1-carboxylic acid, pipecolinic acid, Pro, hydroxypro, azetidine-2-carboxylic acid, Aib, Leu, Ile, Val, Thi, and Phe;

J is selected from the group consisting of Arg, Orn, Asn, Gln, N-$\epsilon$-acetyl-Lys, N-$\delta$-acetyl-Orn, and Lys;

Cn is a hydroxyl group a C-terminal extension such as an amide, alkoxy group, an acidic, basic or neutral aliphatic aromatic, a cyclic amino acid residue of the D- or L-configuration or a peptide extension composed of D- or L-amino acids;

and pharmaceutically acceptable salts thereof.

As used in the specification and claims, "aryl" is an aromatic ring compound such as benzene, phenyl, naphthyl, and substituted forms thereof; and "aralkyl" is an aryl being attached through an alkyl chain, straight or branched, containing from one through six carbons. A "direct bond" is a bond which replaces a particular amino acid compound between adjacent amino acids and which amino acid may also be indicated to be absent by the term "null". The phrase "a suitable amine protecting group" is a group, such as BOC (t-butyloxycarbonyl-) which protects the amine moiety from reaction and which can be removed under mild conditions so as not to affect the rest of the molecule.

Preferred compounds are those in which:

N is hydrogen;

A and B are independently selected from the group consisting of L-Arg, D-Arg, Lys-Lys, Lys;

C and D are independently selected from the group consisting of Pro, dehydropro, and hydroxypro;

E is Gly;

F is selected from the group consisting of Phe, Thi, Leu, and β-cyclohexylalanine;

G is a direct bond or is selected from the group consisting of Ser and Thr;

H is a compound of the D-configuration having the formula selected from the group consisting of:

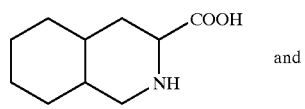

-continued

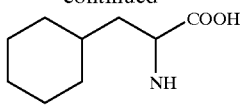

I is selected from the group consisting of Oic, Aoc, Thz, Pro, hype (t-sph), hype (c-sph), hype (c-pr), hype (t-pr), pipecolinic acid, Leu, Phe, Thi, and Tic J is selected from the group consisting of Arg and Lys;

Cn is hydroxyl;

and pharmaceutically acceptably salts thereof.

Most preferred are compounds wherein:

N is hydrogen;

A is D-Arg;

B is Arg;

C is Pro;

D is selected from the group consisting of Pro and HydroxyPro;

E is Gly;

F is selected from the group consisting of Phe, Leu, and Thi;

G is a direct bond or is Ser;

H is a compound of the D-configuration having the formula selected from the group consisting of:

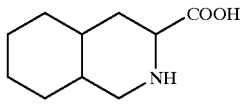 and

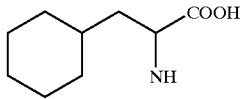

I is Tic, and

J is Arg;

Cn is a hydroxyl group;

and pharmaceutically acceptable salts thereof.

Definitions of the amino acid abbreviations used herein are as follows:

Arg is arginine; Ala is alanine; Aib is 2-aminoisobutyric acid; Aoc is (S,S,S)-2-azabicyclo[3.3.0]octane-3-carboxylic acid; Asn is asparagine; Eac is ε-aminocaproic acid; Gln is glutamine; Gly is glycine; Ile is isoleucine; Leu is leucine; Lys is lysine; Met is methionine; Nal is beta-2-naphthylalanine; Orn is ornithine; Pro is proline; dehydropro is 3,4-dehydroproline; homoPhe is homophenylalanine; hydroxyPro is 4-hydroxyproline; Ser is serine; Thi is beta-2-thienylalanine; Thr is threonine; Thz is thiazolidine-4-carboxylic acid; Phe is phenylalanine; phenylGly is 2-phenylglycine; Tic is 1,2,3,4-tetrahydroisoquinoline-3-carboxylic acid; oic is (2S, 3aS, 7aS)-octahydro-1H-indole-2-carboxylic acid; Val is valine; D-Ric is cis-3-carboxydecahydroisoquinoline.

The following legends have the noted structures:

LEGEND:

Tic = 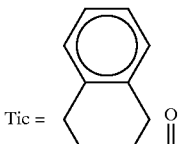

Thz = 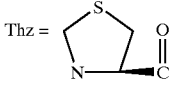

Oic = 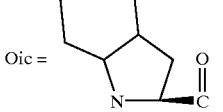

Hype(t-sph) = 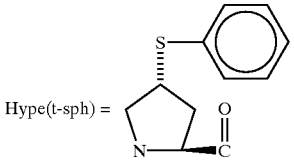

Hype(c-sph) = 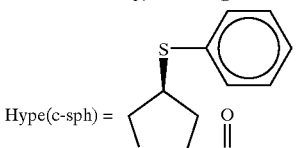

Hype(c-pr) = 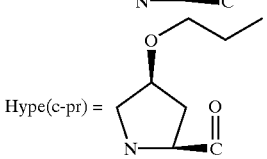

Hype(t-pr) = 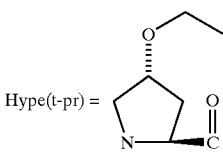

Aoc can be prepared by the method of V. Teetz, R. Geiger and H. Gaul, *Tetrahedron Lett.* (1984), 4479. Tic can be prepared by the method of K. Hayashi, Y. Ozaki, K. Nunami and N. Yoneda, *Chem. Pharm. Bull.* (1983) 31, 312.

All amino acids residues, except Gly, described in the specification are preferably of the L-configuration unless otherwise specified. It would be recognized, however, that the 7 position must always be the D-configuration. The symbols and abbreviations used for amino acids, their derivatives and protecting groups, and peptides and their salts are those customarily used in peptide chemistry. (See *Biochem. J.* (1972), 126:773, which Journal reference is hereby incorporated by reference).

Table I shows the general location of the amino acid groups as used herein.

Particularly preferred modified position (7) compounds are quinoline derivatives, and more particularly, non-aromatic isoquinoline derivatives. Examplary compounds include cis-3-carboxydecahydroisoquinoline having the formula:

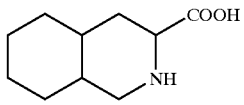

and beta-cyclohexylalanine having the formula:

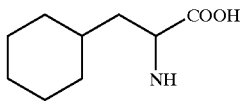

Particularly preferred peptides may be selected from the following materials:
(D) Arg-Arg-Pro-Hyp-Gly-Phe-Ser-(D)Ric-Tic-Arg,
(D) Arg-Arg-Pro-Hyp-Gly-Phe-Ser-(D)Ric-Thz-Arg,
(D) Arg-Arg-Pro-Hyp-Gly-Phe-Ser-(D)Ric-Oic-Arg,
(D) Arg-Arg-Pro-Hyp-Gly-Phe-Ser-(D)Ric-Hype(t-sph)-Arg,
(D) Arg-Arg-Pro-Hyp-Gly-Phe-Ser-(D)Ric-Hype(c-sph)-Arg,
(D) Arg-Arg-Pro-Hyp-Gly-Phe-Ser-(D)Ric-Hype(c-pr)-Arg,
(D) Arg-Arg-Pro-Hyp-Gly-Phe-Ser-(D)Ric-Hype(t-pr)-Arg,
(D) Arg-Arg-Pro-Hyp-Gly-Phe-Ser-(beta-cyclohexylalanine)-Tic-Arg.
(D) Arg-Arg-Pro-Hyp-Gly-Phe-Ser-(beta-cyclohexylalanine)-Thz-Arg,
(D) Arg-Arg-Pro-Hyp-Gly-Phe-Ser-(beta-cyclohexylalanine)-Oic-Arg,
(D) Arg-Arg-Pro-Hyp-Gly-Phe-Ser-(beta-cyclohexylalanine)-Hype(t-sph)-Arg,
(D) Arg-Arg-Pro-Hyp-Gly-Phe-ser-(beta-cyclohexylalanine)-Hype(c-sph)-Arg,
(D) Arg-Arg-Pro-Hyp-Gly-Phe-ser-(beta-cyclohexylalanine)-Hype(c-pr)-Arg, and
(D) Arg-Arg-Pro-Hyp-Gly-Phe-Ser-(beta-cyclohexylalanine)-Hype(t-pr)-Arg.

in the Examples and depicted in the sequences shown below. The starting materials are commercially available and can be prepared by known procedures. Both the cis and trans stereoisomers can be prepared by these means and are within the scope of the present invention with the cis stereoisomer being preferred.

Scheme I

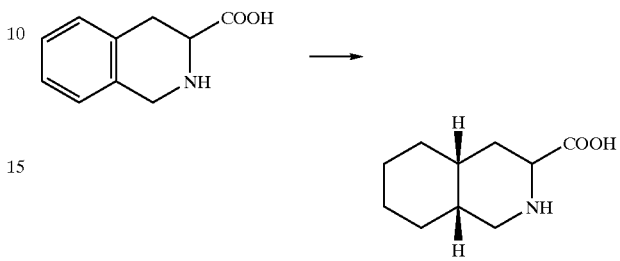

The preparation of compounds for administration in pharmaceutical preparations may be performed in a variety of methods well known to those skilled in the art. Appropriate pharmaceutically acceptable salts within the scope of the invention are those derived from mineral acids such as hydrochloric acid, hydrobromic acid, phosphoric acid, nitric acid and sulfuric acid; and organic acids such as tartaric acid, fumaric acid, lactic acid, ethylsulfonic acid, citric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled

TABLE I

```
N - A - B - C - D - E - F - G - H - I - J - Cn  (formula)
    Arg-Pro-Pro-Gly-Phe-Ser-Pro-Phe-Arg         Bradykinin
     1   2   3   4   5   6   7   8   9          (Position
              SEQ ID NO. 1                       number)
```

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie*, (1974), Vol. 16, parts I & II for solution-phase synthesis, and in *Solid Phase Peptide Synthesis*, (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate non-aromatic isoquinoline derivatives used in the 7-position are prepared by the process described in the art. Merely for purposes of illustration, the class may be said to include mono-, di-, and trialkylamines, such as methylamine, dimethylamine, and triethylamine; mono-, di- or trihydroxyalkylamines such as mono-, di-, and triethanolamine; amino acids such as arginine, and lysine; guanidine; N-methyl-glucosamine; N-methylglucamine; L-glutamine; N-methyl-piperazine; morpholine; ethylenediamine; N-benzyl-phenethylamine; tris(hydroxymethyl) aminomethane; and the like. (See for example, "Pharmaceutical Salts," *J. Pharm. Sci.* (1977) 66(1): 1–19.)

The compounds of the invention may contain an asymmetric carbon atom. Thus, the invention includes the individual stereoisomers, and the mixtures thereof. The individual isomers may be prepared or isolated by methods known in the art.

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation, and swelling.

The therapeutic use of bradykinin antagonists of this invention for other traumatic inflammatory or pathological conditions which are known to be mediated by bradykinin or exacerbated by an overproduction of bradykinin can also be achieved. These conditions include local trauma such as wounds, burns and rashes, angina, arthritis, asthma, allergies, rhinitis, shock, inflammatory bowel disease, low blood pressure, and systemic treatment of pain and inflammation.

In parenteral administration of the novel compounds and compositions of the invention the compounds may be formulated in aqueous injection solutions which may contain antioxidants, buffers, bacteriostats, and so forth. Extemporaneous injection solutions may be prepared from sterile pills, granules, or tablets which may contain diluents, dispersing and surface active agents, binders, and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening and emulsifying agents. The granules or tablets for oral administration may be coated and other pharmaceutically acceptable agents and formulations may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 100 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel compounds are potent, selective bradykinin receptor antagonists.

The following examples are illustrative of preferred embodiments of methods of preparation and compounds of the invention and are not to be construed as limiting the invention thereto.

EXAMPLE 1

This example demonstrates the preparation of cis-3-carboxydecahydroisoquinoline by Scheme I. A mixture of 20 g. 3-carboxy-1,2,3,4-tetrahydroisoquinoline in 300 ml. of 50% ethanol and 5 g. of 5% rhodium-on-alumina catalyst (J. T. Baker Chemical Co.) absorbed three moles of hydrogen at 50–100° and 15 atmospheres. The catalyst was removed by filtration and the filtrate was evaporated in vacuo. The product was recrystallized three times from ethanol, m.p. 256–257°, resulting in a yield of 8.2 g. of product (41%).

Anal. Calcd. for $C_{10}H_{17}NO_2$: C, 65.54; H, 9.55; N, 7.64. Found: C, 65.45; H, 9.35; N, 7.46. The hydrochloride salt was crystallized from ethanolether, m.p. 235–236°.

Anal. Calcd. for $C_{10}H_{17}NO_2.HCl$: C, 54.67; H, 8.26; N, 6.38. Found: C, 54.66; H, 8.49; N, 6.10.

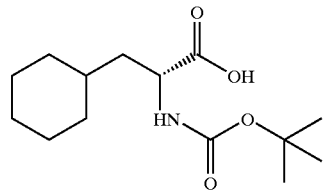

EXAMPLE 2

Preparation of N-Boc-D-cyclohexylalanine

A suspension of D-phenylalanine (5.0 g, 30 mmol) and platinum on activated carbon (10% platinum content, 0.50 g) in aqueous hydrochloric acid (40 mL, 1.0 N) and methanol (4 mL) was shaken at 50 psi of hydrogen at room temperature. After 20 hours, the catalyst was filtered and washed with water. The combined filtrate and washing solvent were concentrated to a white fiberious solid (5.40 g, 86.0%): m.p. 231.5–233.5° C.; $[\alpha]_D$=−21.46 (c=1.01, methanol).

To a stirred suspension of D-cyclohexylalanine hydrochloride (2.62 g, 13.6 mmol), sodium carbonate (3.60 g, 40 mmol), and 2-propanol (10 mL) in water (25 mL) was added di-tert-butyl dicarbonate (3.80 mL, 16.0 mmol). After stirring overnight at room temperature, the suspension was diluted with water (15 mL) and extracted with diethyl ether (2×15 mL). The aqueous layer was acidified to the Congo red indicator endpoint with aqueous hydrochloric acid (5N) and extracted with methylene chloride (3×50 mL). The combined methylene chloride extracts were dried (sodium sulfate) and concentrated to a colorless foam (3.46 g, 94.0%) IR (liquid film) cm−¹ 3425 (broad), 2915, 2843, 1715, 1506, 1393, 1367, 1247, 1164; $^1$H NMR (300 MHz, $CDCl_3$) ppm 0.93 (m, 2H), 1.20 (m, 4H), 1.46 (s, 9H), 1.70 (d, 4H), 4.19 (m, 1H), 4.35 (m, 1H), 4.93 (d, 1H, J=8.1 Hz), 6.20 (br s, 1H, J=4.1 Hz), 9.54 (br s, 1H).$[\alpha]_D$=+16.37 (c=2.05, glacial acetic acid).

EXAMPLE 3

General Procedure for Automated Peptide Synthesis

Preparation of DArg-Arg-Pro-Hyp-Gly-Thi-Ser-D-Ric-Tic-Arg

The peptide was synthesized employing t-Boc chemistry on a solid phase synthesizer (Milligen Biosearch 9600

Peptide Synthesizer). Boc-Arg(Tos)-PAM resin (Applied Biosystems) (PAM=phenylacetamidomethyl), 0.25 g, with a resin substitution of 0.62 mmol Arg/gram of resin, was placed in the reaction vessel and subjected to Procedure A for the coupling of Boc-Oic. Commercially available amino acids were purchased from Bachem Bioscience. Volumes of reagents and solvents were approximately 20 ml/gram of resin.

Procedure A

1. Deprotection: Removal of the t-butyloxycarbonyl-protecting group (Boc) was achieved by treatment of the resin with deblocking reagent (trifluoroacetic acid (TFA)/anisole/dichloromethane(DCM) 45:2.5:52.5 v/v containing 1 mg/mL of indole), two times for one minute and once for twenty minutes. The resin was then washed with DCM several times, followed by neutralization with base [10% diisopropylethylamine (DIEA) in DCM], three times for one minute. The resin was subsequently washed with DCM and dimethylformamide (DMF).

2. Coupling: All couplings and recouplings were mediated in the same manner. Boc-Oic (1.47 mmol, 0.4 M in DMF) was mixed with one equivalent of diisopropylcarbodiimide (DIPCDI) (1.47 mmol, 0.4 M in DCM) for a two minute activation period prior to coupling with the resin. The mixture was added to the reaction vessel containing the resin and mixed for two hours. Coupling efficiency of the amino acid to the growing peptide chain on the resin was checked. Incomplete coupling of an amino acid resulted in a recoupling step. Recoupling involved washing the resin-peptide three times for one minute with base followed by DCM and DMF. Amino acid activation with DIPCDI with addition to the peptide-resin was repeated and allowed to mix an additional two hours. After a successful coupling the peptide-resin was washed several times with DCM.

3. Capping: The growing peptide chain was capped on the a-amino group by acetylation with 1-acetylimidazole (0.3 M in DMF) at the end of each coupling or recoupling. The resin was washed three times with base followed by DCM and DMF. The resin was treated with capping reagent for 30 minutes and then washed with DMF.

Procedure B le;2qThe N-terminal protecting group was removed by the following procedure:

le;2qTerminal deprotection: Following the capping of the final amino acid to be added to the growing peptide chain, the peptide-resin was treated with deblocking reagent (TFA/anisole/DCM) twice for one minute and once for 20 minutes. The resin was washed with DCM followed by methanol and then dried by a stream of inert gas.

le;2qThe following amino acids were added to the growing peptide chain according to the listed programs: Boc-Ser (Bzl) (A), Boc-Thi (A), Boc-Gly (A), Boc-Hyp(Bzl) (A), Boc-Pro (A), Boc-Arg(Tos) (A), Boc-DArg(Tos) (A),(B). This yielded 0.481 g of protected peptide-resin as the TFA salt.

le;2qHF Cleavage: The peptide-resin (0.481 g) was suspended in 5 mL of liquid anhydrous HF (ratio of 10 mL HF/g resin) containing 0.48 mL of anisole at −70° C. and stirred for 60 minutes at 0° C. The HF was removed by a stream of nitrogen gas followed by vacuum (water aspirator). The resin was washed three times with 30 mL of ethyl ether and dried under high vacuum for 30 minutes. The peptide was extracted with distilled deionized water (200 mL) and the solution was lyophilized to give 176 mg of crude deprotected peptide.

le;2qPurification: The peptide was purified on a reverse phase C-18 (2×25 cm) Vydac HPLC column using a gradient of 0.1% TFA/H2O and acetonitrile (0.1% TFA) to give a purified deprotected peptide.

le;2qThe peptide was also characterized by mass spectrometry (JEOL HX110/110 FAB) [M+H] obsd 1308.7, [M+H] calcd 1308.6.

Bradykinin Binding Procedure le;2qBinding of $^3$H-Bradykinin was preformed using the method of D. C. Manning, R. Vavrek, J. M. Stewart, and S. H. Synder, *J. Pharmacol. Exp. Ther.,* (1986), 237, 504. The tissues used in the binding assay were terminal ileum from male Hartley guinea pigs (150–350 g). After dissection, tissues were placed in 20 vol of ice-cold buffer A (25 mM TES containing 0.2 g/L of 1,10-phenanthroline adjusted to pH 6.8 with ammonium hydroxide) and homogenized using a Ploytron Tissumizer at setting 6 for 15 sec. The homogenate was centrifuged at 50,000×g for 10 min, the supernatant discarded, and the pellet resuspended in ice-cold buffer A by homogenization with the Polytron. Each tissue was homogenized and centrifuged three times. The final pellet was resuspended in buffer A containing bovine serum albumin (1 g/L) and Bacitracin (0.14 g/L) to a final volume of 170 mL/g of the original tissue weight. The binding assay consisted of 1 mL in 12×75 mm polypropylene tubes: 50 uL $^3$H-bradykinin (20,000 dpm, ~0.3 nM in the final assay volume), 100 L displacing drug in buffer A, and 750 uL tissue homogenate. Each tray contained tubes, to which no drug was added to measure maximum binding and tubes to which bradykinin (1 uM final concentration) had been added, to measure specific binding. Specific binding accounted for 96–98% total binding. Tubes were incubated for 90 min at ambient temperature. The assays were terminated by filtration over Whatman GF/B glass fiber filters that had been pretreated for 2 hours with polyethyleneimine (2 g/L) using a Brandel Tissue Harvester, followed by washing with 4×1 mL aliquots of ice-cold 50 mM Tris, pH 7.4. Filters were dissolved in Ready-Safe Fluor (Beckman) for at least 90 min before quantitation by liquid scintillation spectrometry. Kd values were determined using saturation binding and analysis by EBDA (G. A. MacPherson, *J. Pharmacol. Methods,* (1985), 213), followed by LIGAND (P. J. Munson, D. Rodbard, *Anal. Biochem.,* (1980), 220). Ki values were determined using competitive analysis followed by EBDA and LIGAND. The following test results were obtained.

| Test Compound | Ki (nM) |
|---|---|
| D-Arg-Arg-Pro-Hyp-Gly-Thi-Ser-(D-Ric)-Tic-Arg | 2.13 | le;2qThe invention being thus described, it will be obvious that the same may be varied in many ways. Such variations are not to be regarded as a departure from the spirit and scope of the invention and all such modifications are intended to be included within the scope of the following claims.

What is claimed is:

1. A peptide having the formula:

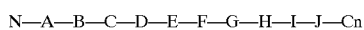

wherein
N is hydrogen;
A is selected from the group consisting of L-Arg, D-Arg, Lys-Lys, L-Lys, and D-Lys;
B is selected from the group consisting of L-Arg, D-Arg, and Lys;
C and D are independently selected from the group consisting of Pro, dehydropro, and hydroxypro;
E is Gly;
F is selected from the group consisting of Phe and Thi;
G is a direct bond or is selected from the group consisting of Ser and Thr;
H is a compound of the D-configuration having the formula selected from the group consisting of:

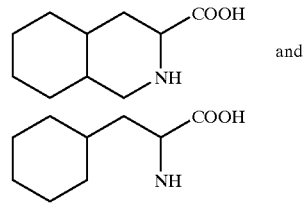

I is selected from the group consisting of Oic, Aoc and Tic;
J is selected from the group consisting of Arg and Lys;
Cn is a hydroxyl group;
and pharmaceutically acceptable salts thereof.

2. A peptide of claim 1 wherein:
N is hydrogen;
A is D-Arg;
B is Arg;
C is Pro;
D is selected from the group consisting of Pro and HydroxyPro;
E is Gly;
F is selected from the group consisting of Phe, Leu and Thi;
G is a direct bond or is Ser;
H is a compound of the D-configuration having the formula selected from the group consisting of:

I is selected from the group consisting of Oic, Aoc, and Tic,
J is Arg;
Cn is a hydroxyl group;
and pharmaceutically acceptable salts thereof.

3. A compound having the formula selected from the group consisting of:

D-Arg-Arg-Pro-Hyp-Gly-Phe-Ser-(D)-Ric-Oic-Arg, and
D-Arg-Arg-Pro-Hyp-Gly-Phe-Ser-(beta-cyclohexylalanine)-Oic-Arg.

4. A compound of claim 1 selected from the group consisting of:

(D) Arg-Arg-Pro-Hyp-Gly-Phe-Ser-(D)Ric-Tic-Arg,
(D) Arg-Arg-Pro-Hyp-Gly-Phe-Ser-(D)Ric-Oic-Arg,
(D) Arg-Arg-Pro-Hyp-Gly-Phe-Ser-(beta-cyclohexylalanine)-Tic-Arg, and
(D) Arg-Arg-Pro-Hyp-Gly-Phe-Ser-(beta-cyclohexylalanine)-Oic-Arg,
wherein (D) Ric is cis-3-carboxydeca-hydroisoquinoline.

* * * * *

UNITED STATES PATENT AND TRADEMARK OFFICE
CERTIFICATE OF CORRECTION

PATENT NO. : 6,458,923 B1
DATED : October 1, 2002
INVENTOR(S) : Donald James Kyle It is certified that error appears in the above-identified patent and that said Letters Patent is hereby corrected as shown below:

Column 15,
Line 28, after "consisting of Pro," and before ";", please replace "dehydropro, and hydroxypro" with -- dehydroPro, and hydroxyPro --.

Signed and Sealed this

Twenty-first Day of January, 2003

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 9
<212> TYPE: PRT
<213> ORGANISM: Mammalian

<400> SEQUENCE: 1

Arg Pro Pro Gly Phe Ser Pro Phe Arg